US008191414B2

(12) United States Patent
Kume et al.

(10) Patent No.: US 8,191,414 B2
(45) Date of Patent: Jun. 5, 2012

(54) SENSOR

(75) Inventors: Makoto Kume, Inuyama (JP); Noboru Matsui, Iwakura (JP)

(73) Assignee: NGK Spark Plug Co., Ltd., Aichi (JP)

( * ) Notice: Subject to any disclaimer, the term of this patent is extended or adjusted under 35 U.S.C. 154(b) by 363 days.

(21) Appl. No.: 12/634,831

(22) Filed: Dec. 10, 2009

(65) Prior Publication Data

US 2010/0139379 A1 Jun. 10, 2010

(30) Foreign Application Priority Data

Dec. 10, 2008 (JP) ................................. 2008-313928

(51) Int. Cl.
*G01M 15/10* (2006.01)
(52) U.S. Cl. ..................................... 73/114.73; 73/23.31
(58) Field of Classification Search .................. 73/23.31, 73/23.32, 31.05, 31.06, 114.73
See application file for complete search history.

(56) References Cited

U.S. PATENT DOCUMENTS

| | | | | |
|---|---|---|---|---|
| 4,556,475 A * | 12/1985 | Bayha et al. | ................... | 204/427 |
| 7,032,433 B2 * | 4/2006 | Hayashi et al. | ............... | 73/31.05 |
| 7,340,942 B2 * | 3/2008 | Matsuo et al. | ............... | 73/31.05 |
| 7,415,877 B2 * | 8/2008 | Okumura et al. | ............... | 73/431 |
| 7,424,819 B2 * | 9/2008 | Fujita et al. | ................... | 73/31.05 |
| 7,430,894 B2 * | 10/2008 | Matsuo et al. | ............... | 73/31.05 |
| 7,568,378 B2 * | 8/2009 | Yoshikawa et al. | ........... | 73/31.05 |
| 2006/0237315 A1 * | 10/2006 | Matsuo et al. | ................. | 204/424 |
| 2006/0288759 A1 * | 12/2006 | Okumura et al. | ............ | 73/31.05 |
| 2007/0119235 A1 * | 5/2007 | Matsuo et al. | ................. | 73/31.05 |
| 2009/0223818 A1 * | 9/2009 | Matsui et al. | ................... | 204/412 |
| 2010/0139364 A1 * | 6/2010 | Kume et al. | ................... | 73/23.31 |

FOREIGN PATENT DOCUMENTS

JP 2007-47093 A 2/2007

* cited by examiner

*Primary Examiner* — Freddie Kirkland, III
(74) *Attorney, Agent, or Firm* — Sughrue Mion, PLLC

(57) ABSTRACT

A sensor including a sensor element including a plurality of electrode terminals, terminal metal fittings, a terminal surrounding member, and lead wires connected to respective terminal metal fittings. The terminal surrounding member is divided into a front side surrounding member and a rear side surrounding member in the front-rear direction, and a rear end face of the front side surrounding member abuts a front end face of the rear side surrounding member. At least one of the terminal metal fittings includes a protruding piece portion protruding in a lateral direction and held between the rear end face of the front side surrounding member and the front end face of the rear side surrounding member.

3 Claims, 14 Drawing Sheets

SIDE VIEW OF SENSOR ELEMENT

SENSOR

BACKGROUND OF THE INVENTION

1. Field of the Invention

The present invention relates to a sensor, and more particularly to a gas sensor including an oxygen sensor, an NOx sensor and an HC sensor for detecting the concentration of a specific gas component in an exhaust gas discharged from an internal combustion chamber, or a temperature sensor for detecting the temperature of an exhaust gas.

2. Description of the Related Art

Sensors are generally used for controlling the air-fuel ratio of a motor vehicle engine, and include a sensor element having electrical properties which change in accordance with the concentration of a specific gas component in the engine exhaust gas (e.g., JP-A-2007-47093). FIG. 15 shows such a gas sensor (hereinafter, also referred to as a sensor) 1. For example, the gas sensor 1 includes a sensor element (hereinafter also referred to as an element) 21 made of a solid electrolyte having oxygen ion conduction properties, a metal shell (a shell main body) 11 for holding the sensor element 21, and a metallic protective sleeve (an outer sleeve) 81 provided on a rear end (an upper end in the figures) side of the metal shell 11. Terminal metal fittings 51 are disposed within the protective sleeve 81 so as to be electrically connected to respective electrode terminals 25 provided on side surfaces of a rear portion of the sensor element 21. Lead wires 61 are connected to clamping portions (barrels) 57 provided at rear ends of the terminal metal fittings 51, respectively. The lead wires 61 pass through respective holes (holes) 105 provided in a sealing elastic member (a grommet or a packing) 101 at a rear end of the protective sleeve 81 so as to be led out from the protective sleeve 81.

In the sensor 1 shown in FIG. 15, the terminal metal fittings 51 and front end portions of the lead wires 61 which are connected to the terminal metal fittings 51 are disposed within terminal holes (spaces) 75 provided in a terminal surrounding member (also referred to as a separator) 71 which is disposed within the protective sleeve 81. The terminal surrounding member 71 is made of an electrically insulating material such as a ceramic. As shown in a cross-sectional view of FIG. 16, the terminal surrounding member 71 has terminal holes (spaces, and hereinafter, also referred to as holes) 75 which extend through the terminal surrounding member 71 in a front-rear direction while ensuring insulation between the terminal metal fittings 51. The terminal metal fittings 51 are accommodated in the respective holes 75. As used herein, the "rear end" denotes an upper end of the sensor 1 shown in FIG. 15 or components thereof, and the "front end" denotes an end (a lower end) opposite the upper end.

The terminal metal fittings 51 of the sensor 1 shown in FIG. 15 are usually formed by pressing or bending a sheet metal material. The terminal metal fitting 51 includes a terminal connecting portion 53 provided in the hole 75. The terminal connecting portion 53 is a plate spring portion which is formed by bending and folding back a front end portion of the terminal metal fitting 51. The terminal connecting portion 53 is pressed against the electrode terminal 25 provided on a side surface of the sensor element 21 positioned in a hole portion provided at a center of the terminal surrounding member 71 by the spring characteristics of the terminal connecting portion 53. Accordingly, the terminal connection portion 53 is electrically connected to the electrode terminal 25. Although not shown in detail, groove-shaped recess portions 71b are formed at a front end 71a of the terminal surrounding member 71. Further, hooks 59, formed at respective front ends of the terminal metal fittings 51 so as to protrude in a lateral direction, are configured to fit in the recess portions 71b.

3. Problems to be Solved by the Invention

In the sensor 1 described above, the hooks 59 provided at the front ends of the terminal metal fittings 51 fit in the recess portions 71b provided at the front end 71a of the terminal surrounding member 71. Consequently, even when the sensor 1 is subjected to an external force which pulls the lead wires 61 and the terminal metal fittings 51 in a rear direction or twists them about axes (imaginary axes) with respect to longitudinal directions of the terminal metal fittings 51, the lead wires 61 and the terminal metal fittings 51 exhibit a certain resistance to the external force and the twisting action. However, this structure can not restrict the terminal metal fittings 51 from moving towards a front end side. In addition, the sensor 1 mounted in an operational motor vehicle is subject to various types of vibration. In these circumstances, firstly, in the sensor 1, the terminal metal fittings 51 may move towards the front end side within the terminal surrounding member 71. Consequently, the position of the terminal metal fittings 51 within the sensor 1 is unstable. Namely, when such movement occurs, reliability in electrical connections between the element 21 and the electrode terminals 25 is reduced, which may result in an electrical connection failure (a contact failure).

Secondarily, although the hooks 59 at the front ends of the terminal metal fittings 51 are still held in the recess portions 71b, when the twisting action or rotating action about the imaginary axis acts on the rear ends of the terminal metal fittings 51, a similar problem as that described above may occur. Namely, since the terminal metal fittings 51 are formed long and narrow, when the rotating action acts on the rear ends of the terminal metal fittings 51, it is not possible to effectively avoid the torsion of a portion of the terminal metal fitting 51 closer to the rear ends thereof than the hooks 59 or a twisted deformation thereof. In such case, an electrical connection failure between the element 21 and the electrode terminals 25 may also occur.

SUMMARY OF THE INVENTION

The invention was made in consideration of the above circumstances. It is therefore an object of the present invention to positively prevent terminal metal fittings from moving not only toward a rear side but also toward a front side within a terminal surrounding member of a sensor. Another object thereof is to prevent the terminal metal fittings from moving in a front-rear direction thereof and to also effectively resist twisting of the terminal metal fittings about imaginary axes thereof extending in the front-rear direction within spaces in a terminal surrounding member, even when the twisting action is received particularly at rear ends or rear portions of the terminal metal fittings.

In a first aspect, the above objects of the present invention have been achieved by providing a sensor extending in a front-rear direction from a front end thereof to a rear end thereof, said sensor comprising: a sensor element extending in the front-rear direction of the sensor and comprising a plurality of electrode terminals; a plurality of terminal metal fittings pressed against and connected to the respective electrode terminals of the sensor element; a terminal surrounding member made of an insulating material and having terminal holes in which the respective terminal metal fittings extend in the front-rear direction, so as to surround the plurality of terminal metal fittings; and a plurality of lead wires connected to the respective terminal metal fittings and which are led out from the rear end of the sensor to an outside thereof, wherein the terminal surrounding member is divided into a front side surrounding member and a rear side surrounding member in the front-rear direction, and a rear end face of the front side surrounding member abuts a front end face of the rear side surrounding member, wherein at least one of the terminal metal fittings comprises a protruding piece portion protruding in a lateral direction and held between the rear end face of the front side surrounding member and the front end face of the rear side surrounding member.

In a second aspect, the present invention provides a sensor according to the first aspect, wherein at least one of the rear end face of the front side surrounding member and the front end face of the rear side surrounding member has a cave-in portion in which the protruding piece portion is fitted so as to restrict the terminal metal fitting comprising the protruding piece portion from rotating around an imaginary axis extending in the front-rear direction within the terminal hole.

In a third aspect, the present invention provides a sensor according to the first aspect, wherein a protruding portion is formed at one of the front side surrounding member and the rear side surrounding member, a recess portion is formed on the other of the front side surrounding member and the rear side surrounding member, and the protruding portion is fitted in the recess portion, whereby the rear end face of the front side surrounding member and the front end face of the rear side surrounding member abut each other so as to prevent one of the front side surrounding member and the rear side surrounding member from rotating relative to the other about an axis of the sensor.

According to the first aspect of the invention, the protruding piece portion of the terminal metal fitting is held by the rear end face of the front side surrounding member and the front end face of the rear side surrounding member. Consequently, in the sensor, the terminal metal fittings can be prevented from moving not only in a rear direction relative to the terminal surrounding member but also in a front direction (towards a front end side). Therefore, the positions of the terminal metal fittings can be stabilized within the terminal surrounding members to an extent that the terminal metal fittings are prevented from moving in both directions. Further, it is possible to prevent electrical connection failures or contact failures between the terminal connecting portions of the terminal metal fittings and the electrode terminals of the sensor element. In this aspect, although all the terminal metal fittings preferably include the protruding piece portion, not all the terminal metal fittings need include the protruding piece portion. Even though only one of the terminal metal fittings includes the protruding piece portion, the advantage with respect to the terminal metal fittings can be obtained.

In the sensor according to the second aspect of the invention, in addition to the advantage obtained by the first aspect, the following advantage can be obtained. In this aspect, since the protruding piece portion on the terminal metal fitting fits in the cave-in portion (the cave-in portion for preventing rotation of the terminal metal fitting), even when the rear end of the terminal metal fitting or the lead wire which is connected thereto is twisted, the twisting action is interrupted by the protruding piece portion. That is, a portion of the terminal metal fitting which is continuous from the protruding piece portion towards the front end side thereof can be restricted from rotating about the imaginary axis extending in the front-rear direction within the hole. By providing the terminal connecting portion of the terminal metal fitting on the portion on the front end side of the terminal metal fitting which is continuous from the protruding piece portion or providing the protruding piece portion further rearward than the terminal connecting portion, the occurrence of an electrical connection failure between the terminal connecting portion and the electrode terminal of the element can be prevented more effectively. In the second aspect of the invention, with respect to the "cave-in portion," the phrase "at least one of the rear end face of the front side surrounding member and the front end face of the rear side surrounding member" means that the cave-in portion may be formed on one of the rear end face of the front side surrounding member and the front end face of the rear side surrounding member, or may be formed on both the rear end face of the front side surrounding member and the front end face of the rear side surrounding member.

According to the sensor of the third aspect of the invention, one of the front side surrounding member and the rear side surrounding member is prevented from rotating relative to the other of the front side surrounding member and the rear side surrounding member about the axis of the sensor. Consequently, in addition to the advantages described above, the position of the terminal metal fitting having the protruding piece portion is held in the terminal surrounding member in a more stable manner.

DETAILED DESCRIPTION OF THE PREFERRED EMBODIMENTS

Hereinafter, preferred embodiments of the invention will be described in detail with reference to FIGS. 1 to 11. However, the present invention should not be construed as being limited thereto.

Figure 1:
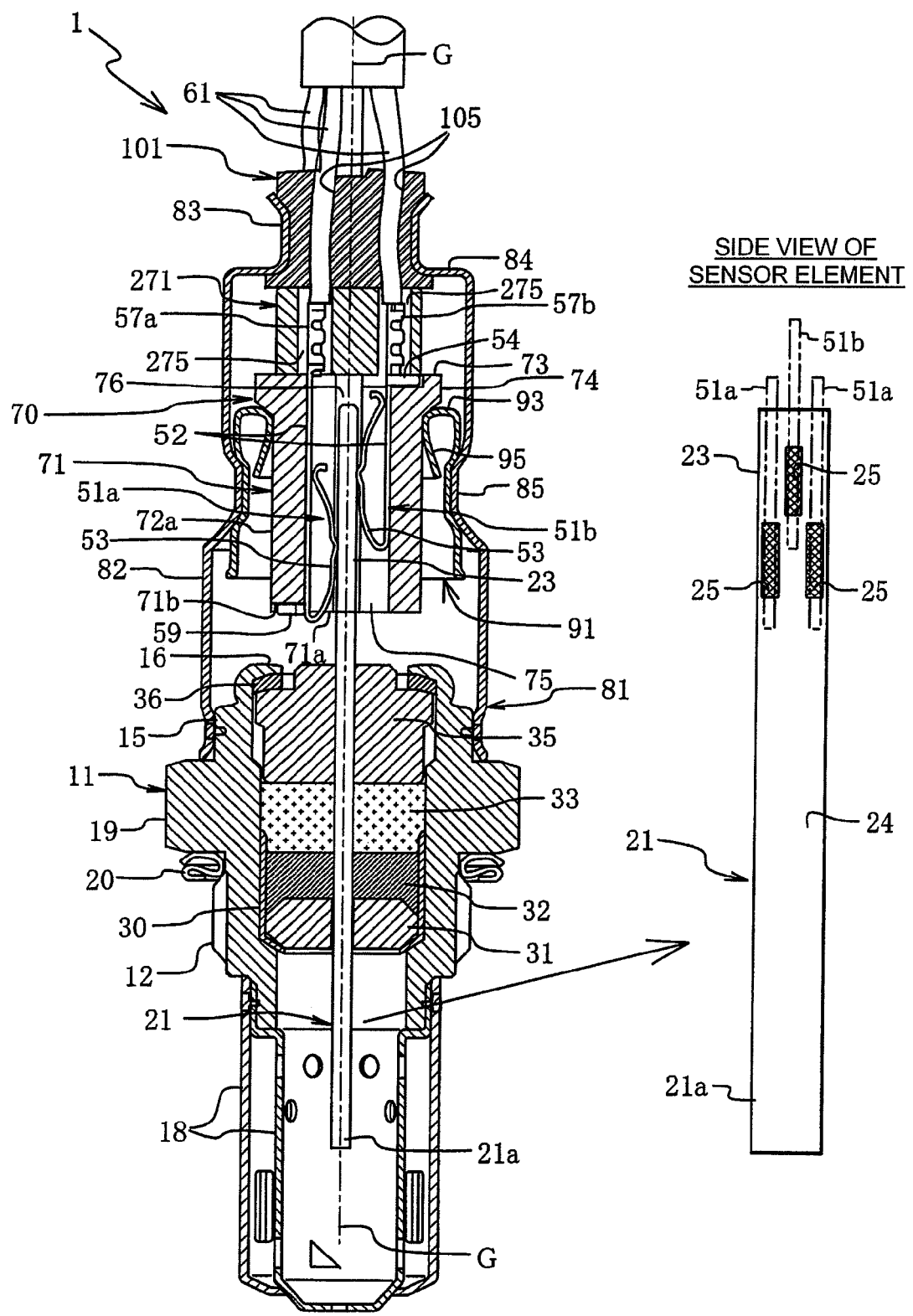
FIG. 1 is a front vertical sectional view showing a sensor of an embodiment and a right or left side view of a sensor element.
Figure 2:
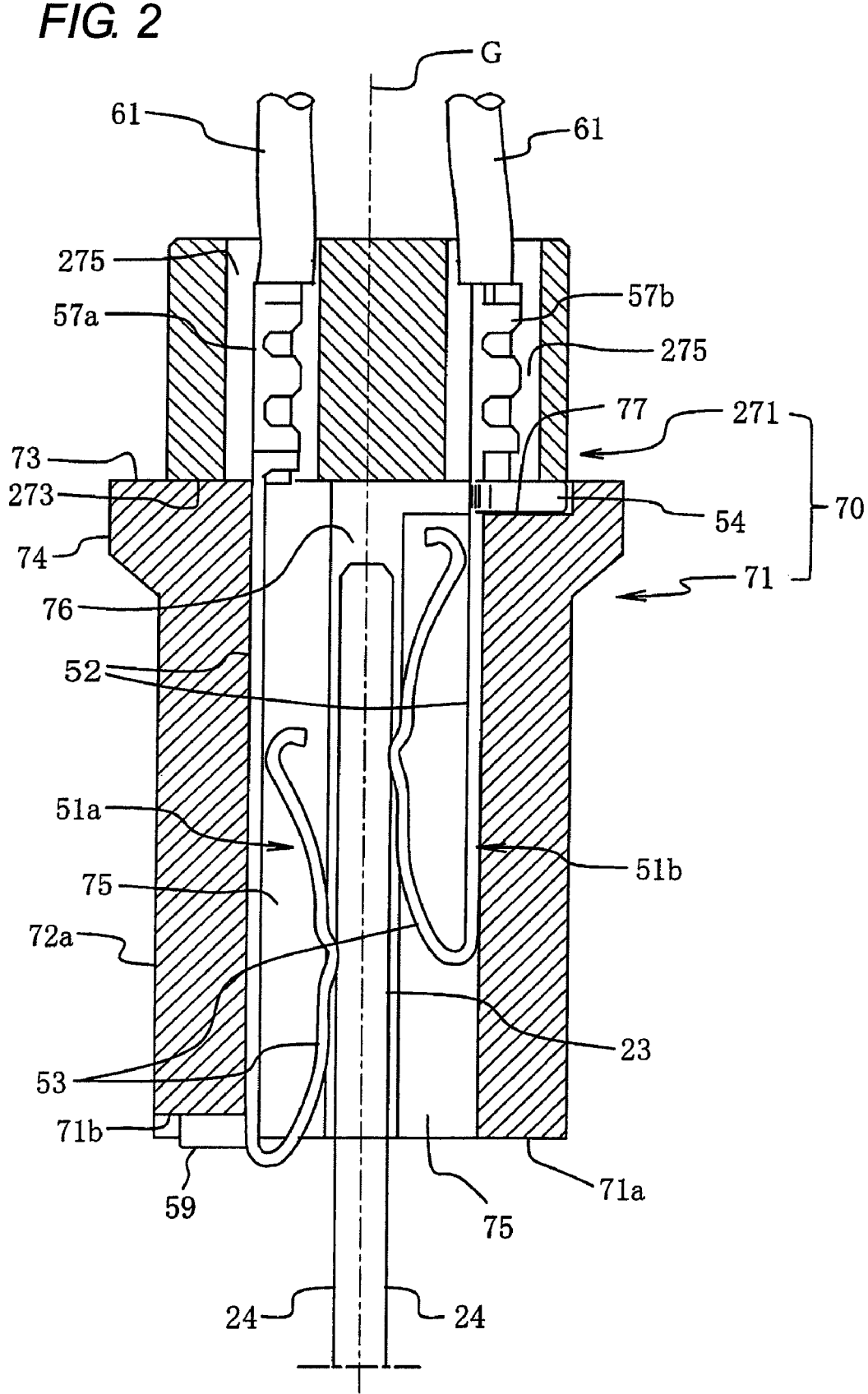
FIG. 2 is an enlarged view of a main part of FIG. 1.
Figure 15:
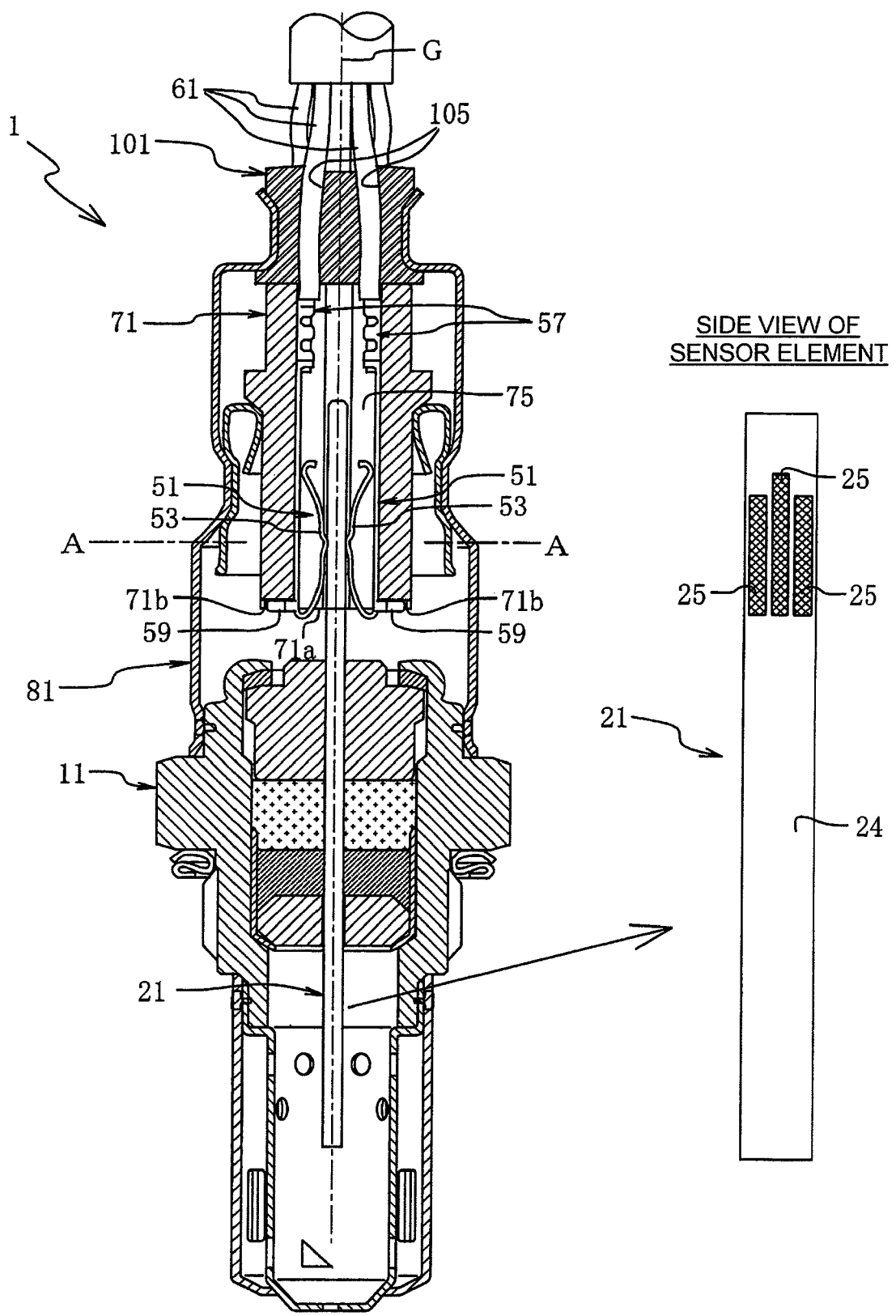
FIG. 15 is a front vertical sectional view illustrating a conventional sensor and a side view of a sensor element in the front vertical sectional view.
Figure 16:
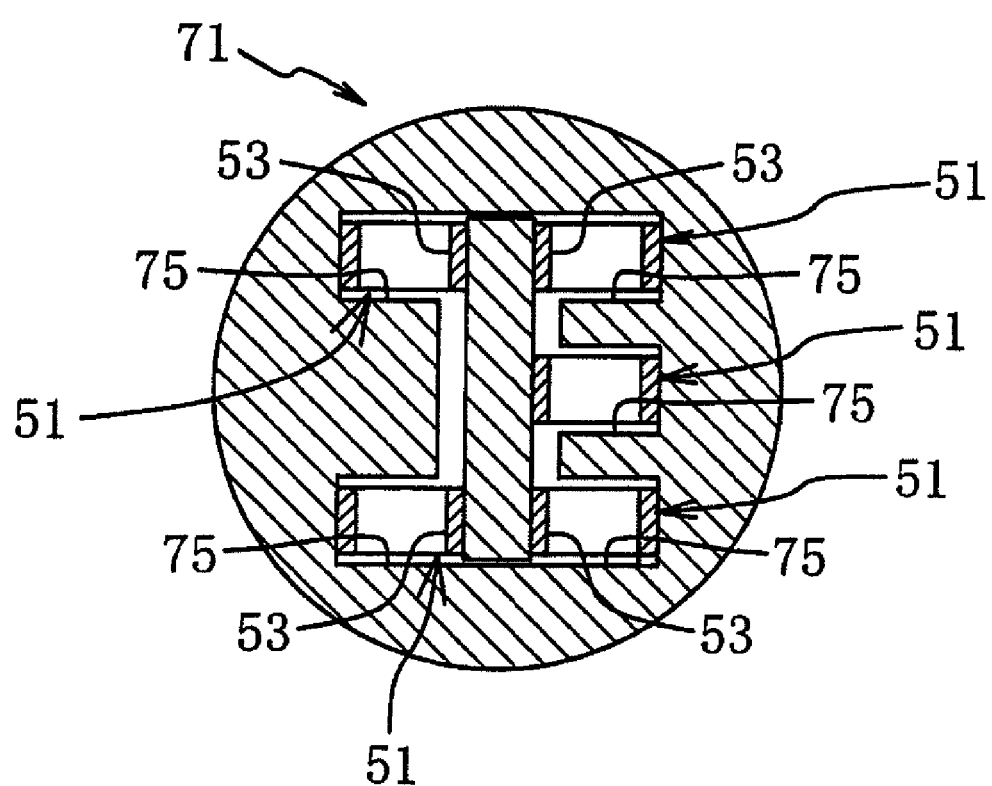
FIG. 16 is a cross-sectional view of a terminal surrounding member taken along the line A-A of FIG. 15.

A sensor according to an embodiment of the invention is an oxygen sensor 1 (hereinafter, also referred to as a sensor 1) for detecting the concentration of oxygen contained in exhaust gas and basically differs from the sensor shown in FIG. 15 in the following points. At first, a main part of the sensor of the embodiment will be schematically described based on these different points. Namely, as shown in FIGS. 1, 2 and the like, in the sensor 1 of this embodiment, a terminal surrounding member 70 made of an insulating material is divided into a front side surrounding member 71 and a rear side surrounding member 271 in a front-rear direction, and a rear end face 73 of the front side surrounding member 71 and a front end face 273 of the rear side surrounding member 271 abut each other. A protruding piece portion 54 is provided on a terminal metal fitting 51b as shown in a right side in FIGS. 1 and 2. This protruding piece portion 54 is held (sandwiched) between the rear end face 73 of the front side surrounding member 71 and the front end face 273 of the rear side surrounding member 271.

Figure 3:
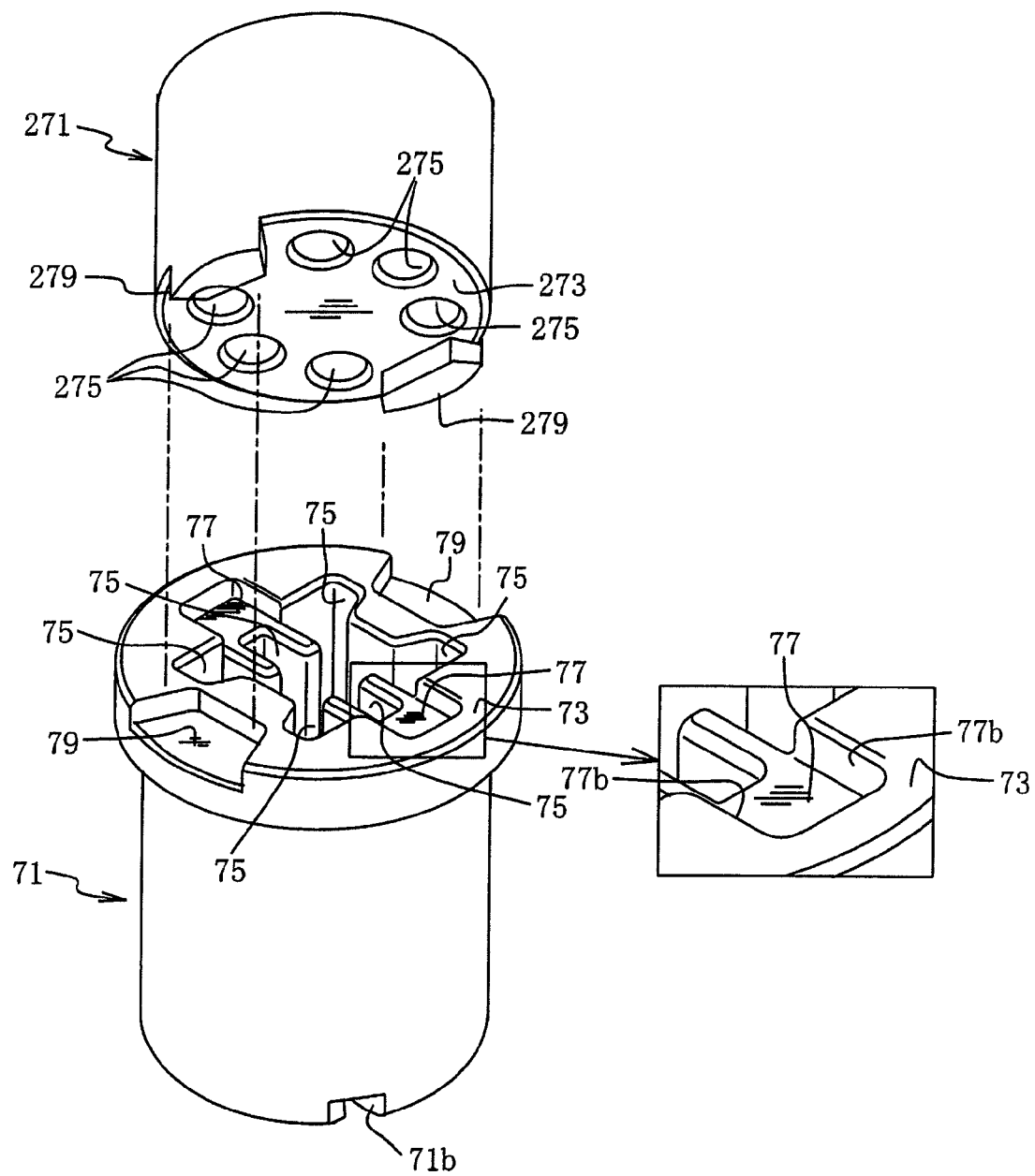
FIG. 3 is a drawing illustrating a front side surrounding member and a rear side surrounding member used in the sensor of FIG. 1, a lower part being a perspective view of the front side surrounding member as viewed from a rear end side, and an upper part being a perspective view of the rear side surrounding member as viewed from a front end side.
Figure 4:
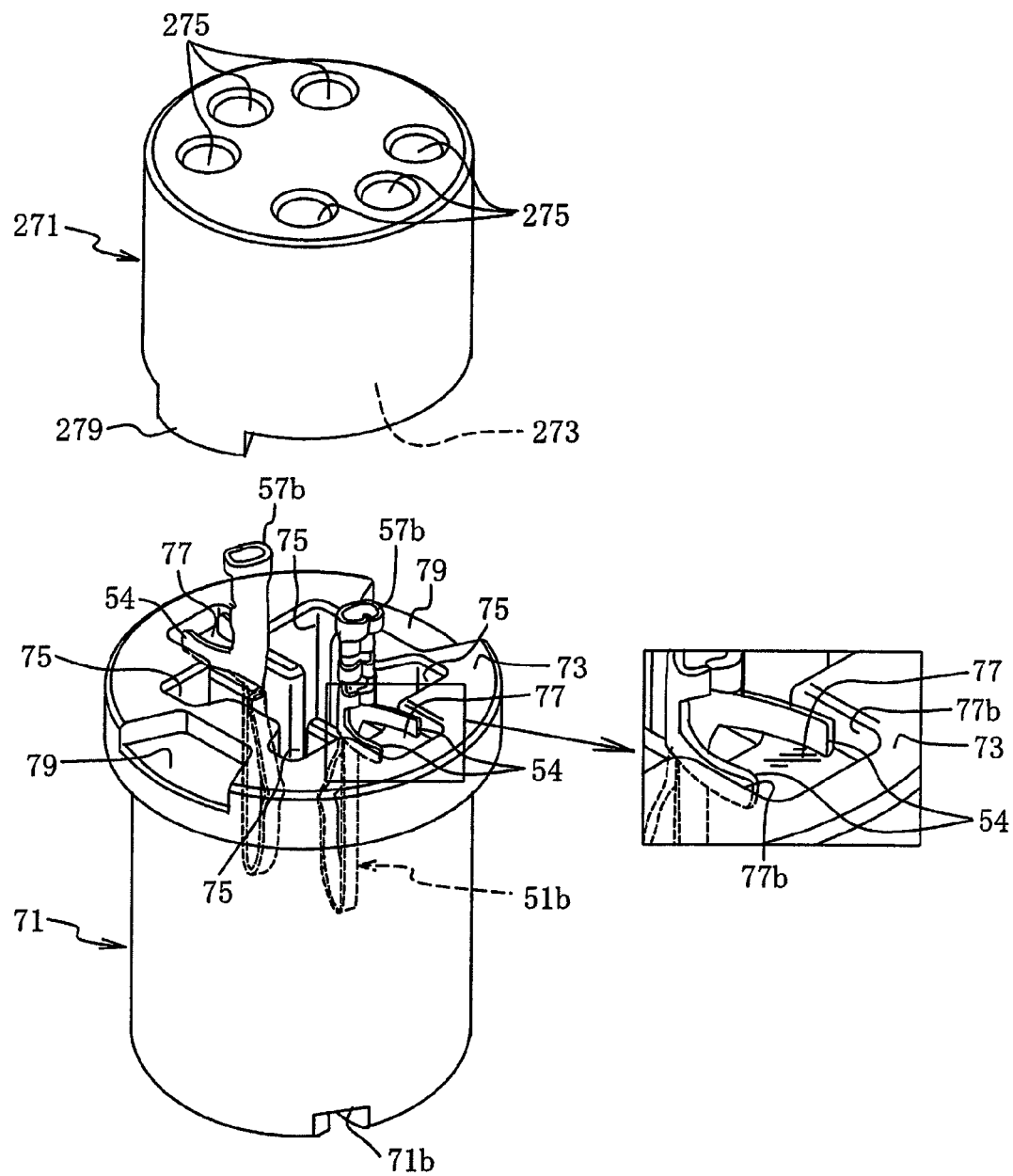
FIG. 4 is an exploded perspective view as viewed from the rear end side which illustrates the front side surrounding member and the rear side surrounding member which are used in the sensor of FIG. 1.
Figure 5:
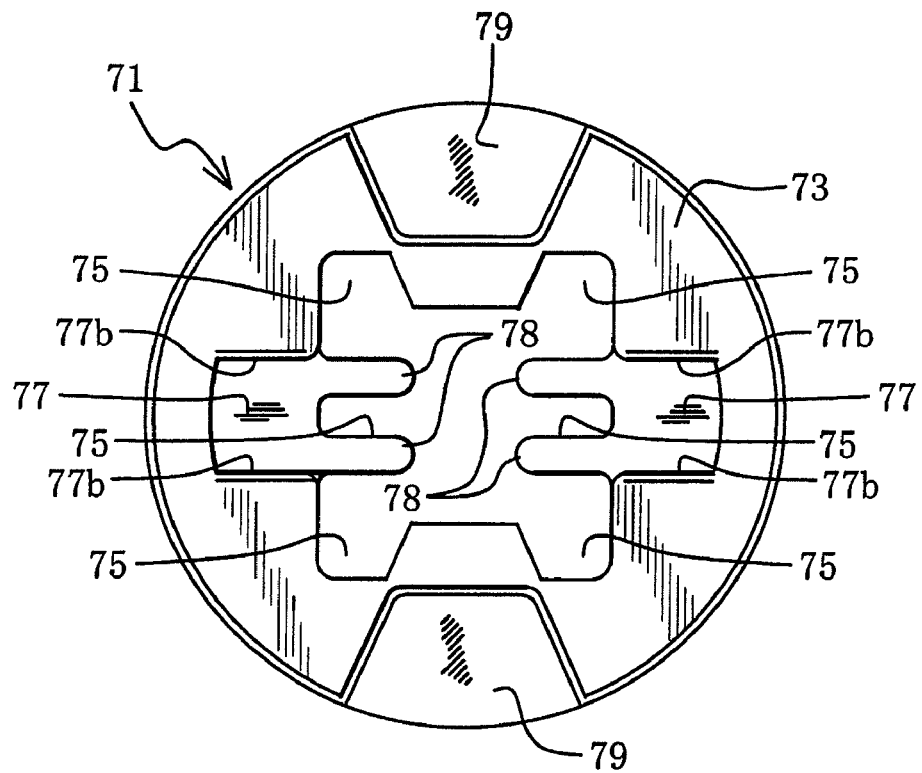
FIG. 5 is a view of the front side surrounding member, as viewed from a rear end face side, which is used in the sensor of FIG. 1.
Figure 6:
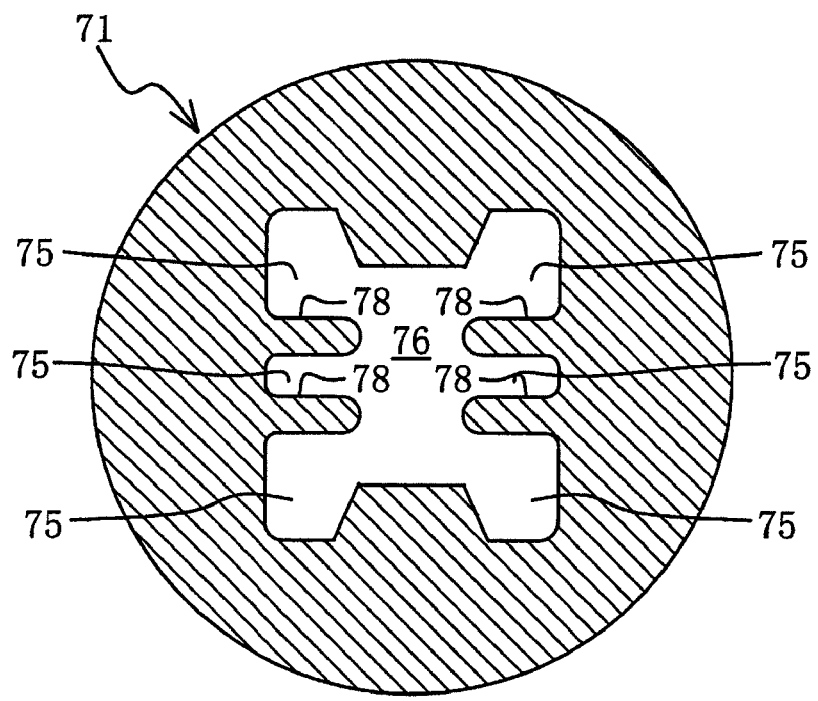
FIG. 6 is a cross-sectional view of the front side surrounding member.

In this embodiment, cave-in portions 77 are formed on the rear end face 73 of the front side surrounding portion 71. As shown in FIGS. 2 to 4 and the like, the protruding portions 54 of the terminal metal fitting 51b are fit into the corresponding cave-in portions 77. Further, the terminal metal fittings 51b which have the protruding piece portions 54 are restricted from rotating about their imaginary axes (not shown) extending in a front-rear direction within corresponding terminal holes 75 in a state in which the protruding piece portions 54 fit in the corresponding cave-in portions 77. In this embodiment, when viewed from the top at the rear end face 73 (when viewed from a rear end side, see FIGS. 5 and 7), the cave-in portions 77 are recessed so as to be formed into a rectangular shape in a radially outward direction, and the protruding piece portions 54 of the terminal metal fittings 51b fit in the cave-in portions 77. As described below, in this embodiment, three terminal metal fittings are disposed on each of side surfaces (left and right sides in FIGS. 1 and 2) 24 of an element 21 so as to face each other across the element 21. In this manner, element 21 having an axis G is held between opposing terminal metal fittings on left and right sides thereof within the terminal surrounding member 70. A terminal connecting portion 53 is disposed in each hole 75 so as to be pressed against a corresponding electrode terminal 25 by making use of its spring characteristics. Terminal metal fittings 51b which are positioned centrally on the respective side surfaces 24 have protruding piece portions 54, and the protruding piece portions 54 are configured to fit in the recess portions 77 on the rear end face 73 of the front side surrounding member 71.

Consequently, the above described configuration of the sensor 1 prevents the terminal metal fittings 51b from moving not only in a rear direction, but also in a front direction. Since the protruding piece portions 54 of the terminal metal fittings 51b fit in the corresponding cave-in 77 as described above, even when the rear ends of the terminal metal fittings 51b or lead wires 61 connected thereto are twisted, rotation of the terminal metal fittings 51b about their imaginary axes, which extend in the front-rear direction within the holes 75 in the terminal surrounding member 70 in which they are disposed, is prevented.

Hereinafter, the sensor 1 of the embodiment will be described in greater detail by reference to FIGS. 1 to 11. Firstly, an overall configuration of the sensor 1 will be described. In this sensor 1, the sensor element 21 is formed mainly from a ceramic into a long strip-like shape having a rectangular cross section and includes a detecting portion (not shown) 21a on a front end side (a lower end side in the figures). The sensor element 21 is disposed inside a cylindrical metal shell 11 (hereinafter, also referred to as a main body 11) and is fixed in place therein in a condition in which airtightness is held. The metal shell 11 is formed into a concentrically stepped cylindrical shape in which its inner circumferential surface increases in diameter sequentially from a front end (a lower end in FIG. 1) towards a rear end thereof, and fixing threads 12 for mounting to an exhaust pipe (not shown) are formed on an outer circumferential surface at a portion close to the lower end.

An airtightness holding and fixing means for fixing the element 21 while maintaining airtightness is provided on an outer side of the element 21 inside the main body 11 so as to be filled therebetween. This airtightness holding and fixing means is made up of a holder 31 made of alumina and sealing materials (talc in this embodiment) 32, 33 disposed sequentially in that order from the bottom on an inner collar supported inside a tubular member 30 which is interposed at a lower step portion inside the main body 11. A sleeve 35 is disposed on the seal material 33. By inwardly bending a thin crimping cylindrical portion 16 (which is provided so as to extend continuously from a cylindrical portion 15 positioned at a portion of the main body 11 which lies near the rear end thereof) and compressing a rear end of the sleeve 35 towards a front end side of the main body 11 via a ring washer 36 so as to compress the inner sealing materials 32, 33, the element 21 is fixed inside the metal shell 11 in an airtight fashion.

The front end side of element 21 in which the detecting portion 21a is provided protrudes a predetermined amount (length) from a front end face of the main body 11, while a portion of the element 21 which is positioned near a front end (an upper end in FIG. 1) thereof or a rear portion 23 of the element 21 protrudes a predetermined amount (length) from the rear end of the main body 11 and a rear end face of the sleeve 35. A protector (a protective cover) 18 provided with a plurality of holes (vent holes) and having a double-layer construction is placed on a rear end (the detecting portion 21a) of the element 21 so as to surround the periphery thereof, and the protector 18 is fitted on the front end of the main body 11 and is fixed thereto. A large diameter portion 19 is formed on an outer circumference of the main body 11 at an intermediate portion in the direction of the axis G thereof so as to protrude therefrom, and this large diameter portion 19 constitutes a polygonal portion (a tool engagement portion) which is used to screw the main body 11 into the exhaust pipe (not shown). Also, a sealing gasket 20 is attached to a lower surface thereof.

A plurality of (for example, three) electrode terminals (metallized layers) 25 are formed side by side, as shown on the right side of FIG. 1, on each of side surfaces 24, 24 of the rear portion 23 of the element 21 closer to the rear end side. The element 21 is disposed and fixed within the main body 11 as described above, and protrudes from a rear end (an upper end in the figure) of the sleeve 35 (see a right side drawing in FIG. 1). In this embodiment, however, an electrode terminal 25 which is positioned centrally between electrode terminals 25 which are positioned on both lateral edges of the side surface 24, is positioned further rearward (upwards in the figure) than those on the lateral edges. In this manner, the central electrode terminal 25 and the electrode terminals 25 on the lateral edges are formed in positions which are not superposed one on top of the other in the front-rear direction (in a vertical direction in the figure). These electrode terminals 25 are provided for picking up a detected output from the detecting portion 21a and for applying a voltage to a heater, not shown, which is formed on the element 21. The electrode terminals 25 are formed by calcining together with the element 21.

Figure 14:
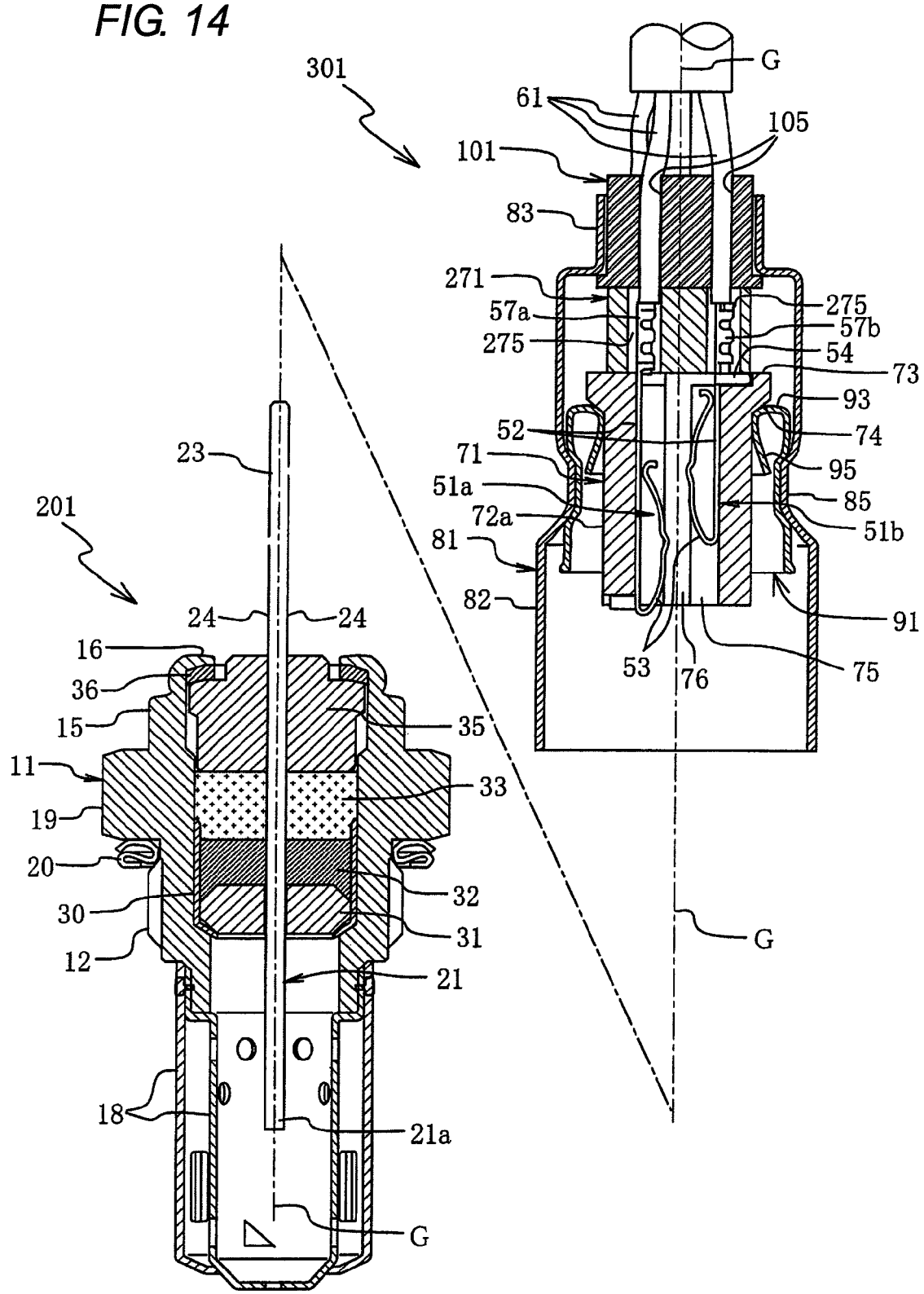
FIG. 14 is a drawing illustrating a step of fabricating the sensor of FIG. 1.

Thus, what has been described heretofore is a substantially front end side half part (a substantially lower half part of FIG. 1) of the sensor 1 of the embodiment, and corresponds to an element side assembly half 201, shown in a bottom left part of FIG. 14, in which the element 21 is fixed within the main body 11. The sensor 1 of the embodiment is fabricated by assembling together the element side assembly half 201 and a terminal metal fitting side assembly half 301, shown in a top right part of FIG. 14, which constitutes a substantially rear end side half part (a substantially upper half part of FIG. 1) of the sensor 1 as described below. Next, The substantially rear end side half part of the sensor 1 which constitutes the terminal metal fitting side assembly half 301 will be described in detail.

Namely, a cylindrical protective sleeve 81 having different diameters is disposed on a rear end side of the sensor 1, and the terminal surrounding member 70, which is made of an insulating material (a ceramic) and which has a circularly tubular or cylindrical shape, is disposed coaxially with the metal shell 11 at the rear portion 23 of the element 21 inside the protective sleeve 81. Although described in detail below, the terminal metal fittings 51b and terminal metal fittings 51a are disposed within the terminal surrounding member 70 and are electrically connected to the electrode terminals 25 on respective side surfaces 24 of the element 21, respectively, with their terminal connecting portions 53 pressed against the corresponding electrode terminals 25. The terminal surrounding member 70 is divided in the front-rear direction into the rear side surrounding member 71 which is positioned on the front end side (the lower side in FIG. 1) and the rear side surrounding member 271 which is positioned on the rear end side. The front side surrounding member 71 and the rear side surrounding member 271 are disposed coaxially with the front end face 273 of the rear side surrounding member 271 abutting the rear end face 73 of the front side surrounding member 71 (see FIGS. 1 and 2).

Next, configurations of the front side surrounding member 71 and the terminal metal fittings 51a, 51b will be described in detail by reference to FIGS. 1 to 7 and the like. The front side surrounding member 71 has a circular ring-like flange 74 on an outer circumference of a rear end portion thereof and is formed into a substantially cylindrical shape. The front side surrounding member 71 has a hole portion 76 which extends therethrough in the front-rear direction at a center thereof through which the axis G passes, and the rear portion 23 of the element 21 is inserted into this hole portion 76. In a cross section thereof (see FIG. 6), a plurality of terminal holes 75 are provided in the front side surrounding member 71 so as to extend therethrough in the front-rear direction on each side of the hole portion 76. The terminal metal fittings 51a, 51b are inserted into these terminal holes 75 so as to hold the element 21 therebetween. However, the individual terminal holes 75 are divided by walls (bulkheads) 78 (see FIGS. 5 and 6) which extend in the front-rear direction so as to ensure electrical insulation between the adjacent terminal metal fittings 51a, 51b. The terminal metal fittings 51a, 51b are disposed in the corresponding terminal holes 75 and are electrically connected to the corresponding electrode terminals 25 on the element 21 which is disposed in the central hole portion 76.

Figure 7:
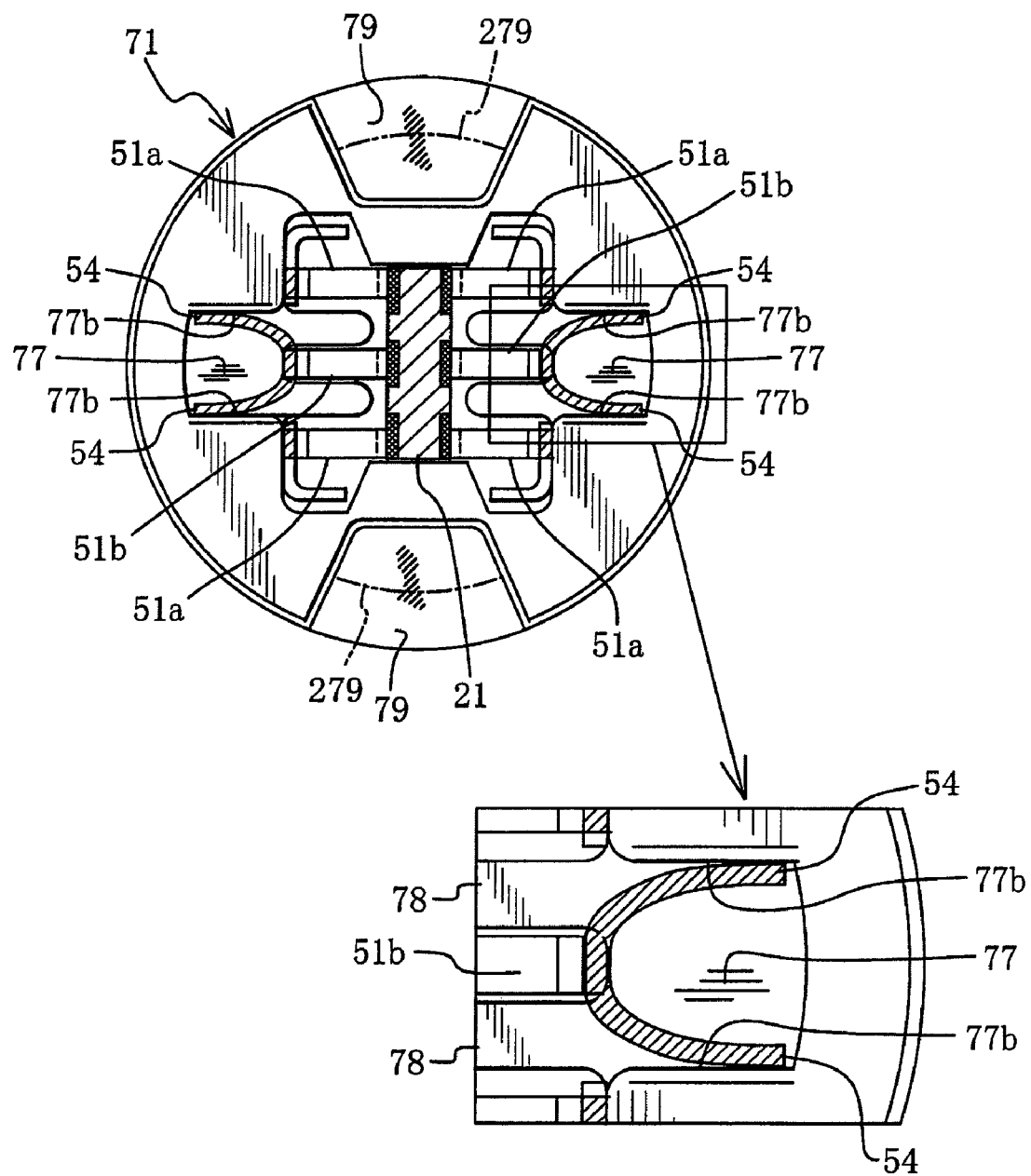
FIG. 7 is a view of the front side surrounding member shown in FIG. 5 in which terminal metal fittings are disposed within holes.
Figure 10:
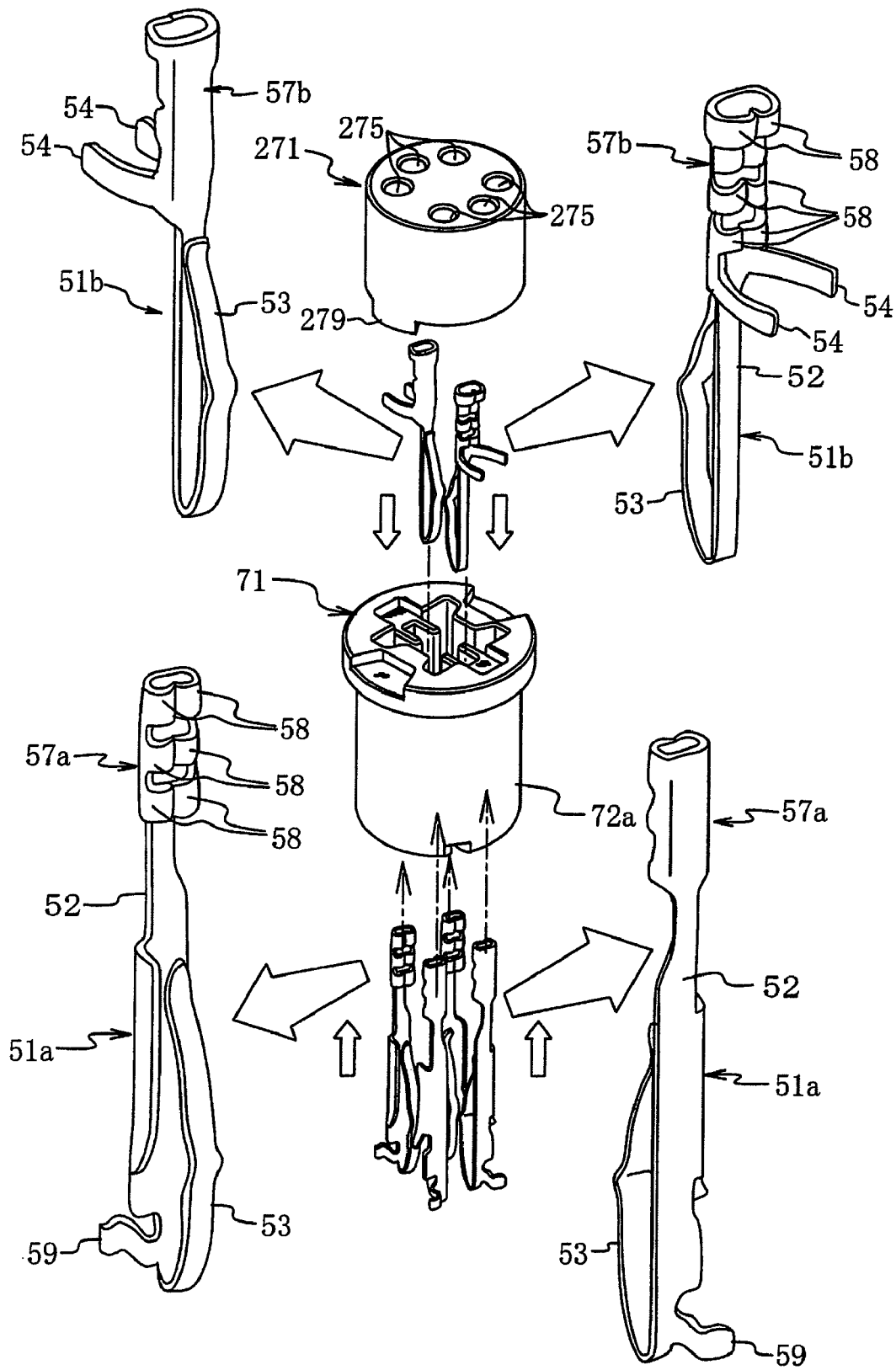
FIG. 10 is an exploded perspective view which illustrates a main part of the invention.
Figure 11:
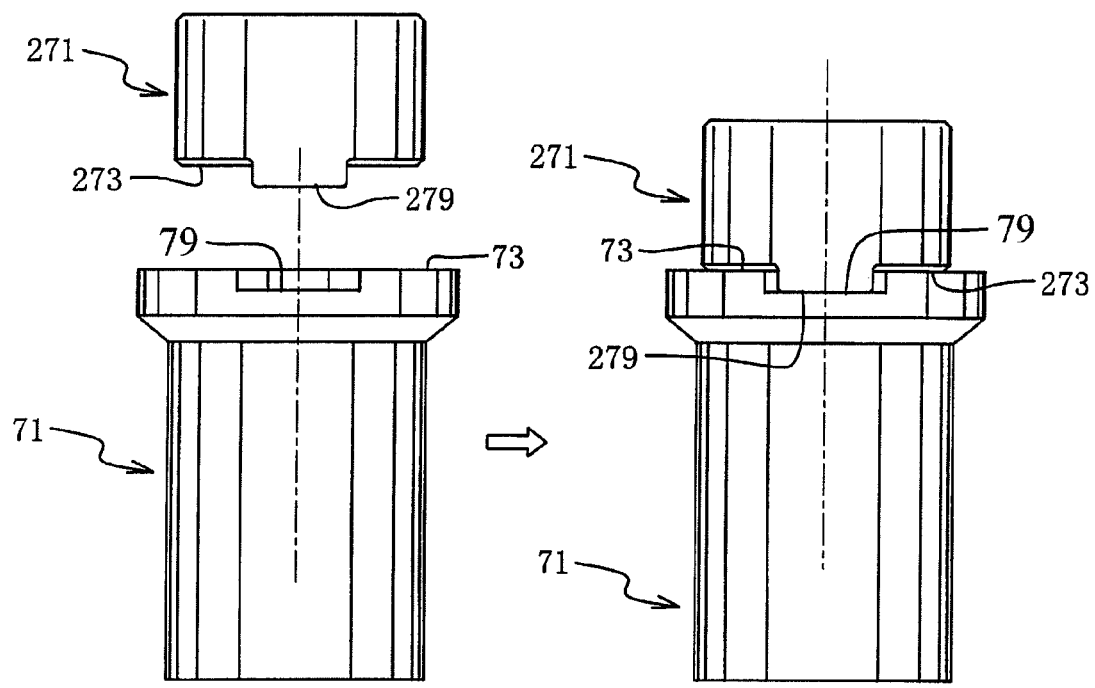
FIG. 11 is a drawing illustrating a step of abutting a front end face of the rear side surrounding member to a rear end face of the front side surrounding member.

In this embodiment, the individual terminal metal fittings 51a, 51b each include the terminal connecting portion 53 which has spring characteristics and which is bent in a foldback fashion at a front end of a terminal metal fitting main body (a relay wire portion) 52. The connecting portion 53 extends in the front-rear direction into an arc-like shape which is made convex on a side facing the element 21. The terminal connecting portions 53 are then pressed against the corresponding electrode terminals 25 on the respective side surfaces 24 of the element 21 by making use of their spring characteristics within the corresponding terminal holes 75. In this embodiment, as shown in FIGS. 7 and 10 and the like, with respect to one of the groups of terminal holes 75 (which are disposed on the sides of the front side surrounding member 71 and which face each other across the element 21), the metallic terminals 51a disposed in the terminal holes 75 arranged on outer sides (lateral edge sides) in a width direction of the element 21 are made different from the terminal metal fitting 51b disposed in the centrally located terminal hole 75 (see FIG. 10). This central terminal metal fitting 51b is provided with the protruding piece portion 54 which protrudes in a bifurcated fashion towards an opposite side to the element 21 (outwards) in a position lying further rearward than the terminal connecting portion 53.

Here, the terminal metal fittings 51a, 51b which are disposed in the sensor 1 of the embodiment will be described in greater detail (see FIG. 10). In these terminal metal fittings, the terminal elements 51a which are disposed in the terminal holes 75 on each side of the front side surrounding member 71 arranged on both outer sides (the lateral edge sides) in the width direction of the element 21, are different in shape and size from the terminal metal fitting 51b which is disposed in the central terminal hole 75. In FIGS. 1 and 2, the terminal metal fitting 51a which is shown as being positioned on a left side of the axis G is one of the terminal metal fittings 51a positioned at both lateral edge sides, and the terminal metal fitting 51b which is shown as being positioned on a right side of the axis G is the central terminal metal fitting 51b. The terminal connecting portion 53 of the central terminal metal fitting 51b is formed shorter than those of the outer terminal metal fittings 51a.

Further, these terminal metal fittings 51a, 51b all include clamping portions (barrels) 57a, 57b for clamping the lead wires 61 for connection at their rear ends or rear portions. However, the terminal metal fittings 51a, 51a which are positioned on the lateral edge sides are different from the terminal metal fitting 51b which is positioned at the center with respect to orientation of the barrels. Namely, in the terminal metal fittings 51a, 51a which are positioned on the lateral edge sides, crimping pieces 58 which constitute the clamping portions 57a, 57a are bent towards the element 21 side (the electrode terminal side) so as to clamp the lead wires (front ends of core wires) 61 for connection.

On the other hand, in the central terminal metal fitting 51b, a crimping piece which constitutes the clamping portion 57b is bent towards a side opposite the electrode terminal 25 so as to clamp the lead wire 61 for connection. The terminal metal fittings 51a, 51a which are positioned on the lateral edge sides include at their front ends protruding hooks (lances) 59. The hooks 59 are locked in groove-like recess portions 71b on a front end face 71a of the front side supporting member 71 so as to prevent rearward movement of the terminal metal fittings 51a, 51a. Further, as shown in FIG. 10, the portions of the terminal metal fittings 51a, 51a which are positioned on the lateral edge sides where the terminal metal fitting main bodies 52 reside are bent on an outer side in an angle-like fashion.

Figure 8:
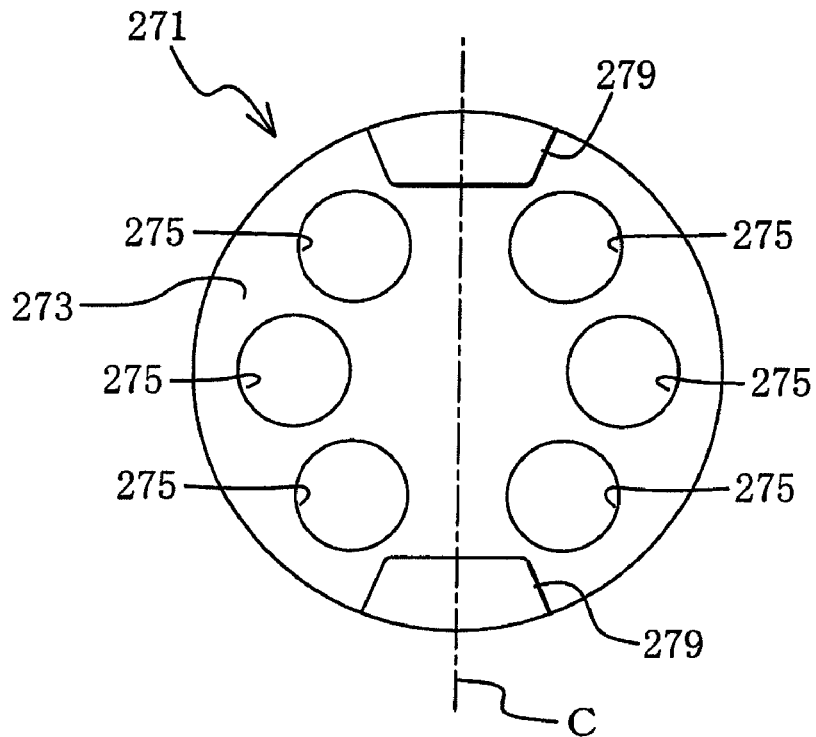
FIG. 8 is a view of the rear side surrounding member, as viewed from a front end face side, which is used in the sensor of FIG. 1.
Figure 9:
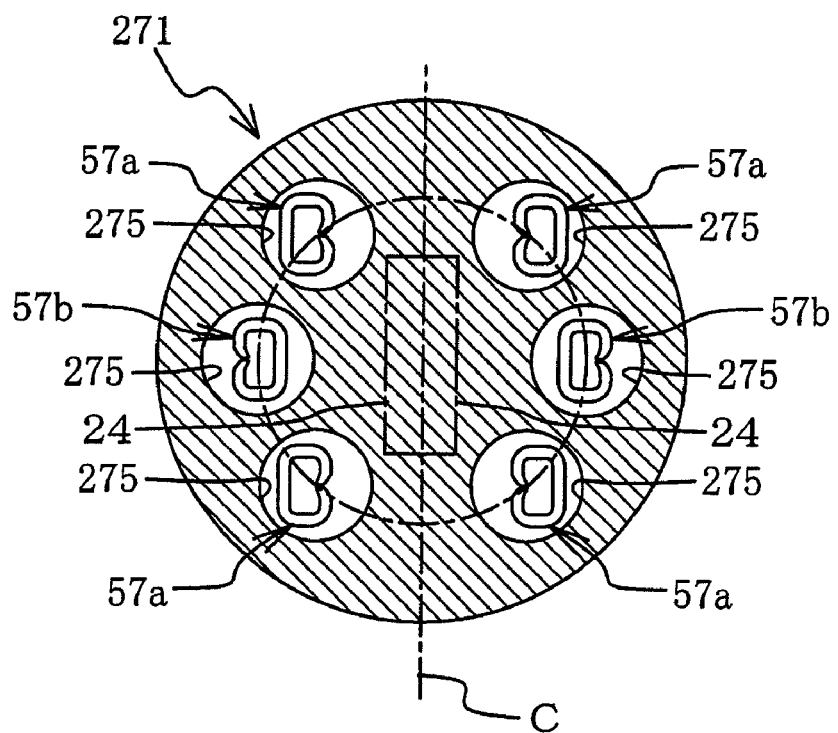
FIG. 9 is a cross-sectional view of the rear side surrounding member.

Next, the rear side surrounding member 271 will be described (see FIGS. 2 to 4, 8 and 9). This rear side surrounding member 271 has a cylindrical shape and includes terminal holes 275 which extend therethrough in the front-rear direction thereinside. The terminal holes 275, arranged, in plan view, correspond to the terminal holes 75 in the front side surrounding member 71 and the clamping portions 57a, 57b of the terminal metal fittings 51a, 51b. Consequently, the terminal hole 275 which accommodates the clamping portion 57b of the terminal metal fitting 51b which is disposed at the center is offset outwards at the terminal holes 275 which are positioned on lateral edge sides relative to a center line C held by both side surfaces 24 of the element 21 when viewed from a rear end side as shown in FIGS. 8 and 9. Inside diameters of the individual terminal holes 275 in the rear side surrounding member 271 are of such a size to allow passage of the clamping portions 57a, 57b which clamp the lead wires 61. Further, the terminal holes 275 have a circular cross section.

The rear end face 73 of the front side surrounding member 71 is formed as described below. Namely, as shown in FIGS. 3, 4 and the like, the cave-in portion 77, into which the protruding piece portion 54 can fit, is formed to extend in a radially outward direction while being recessed towards the front end 71a side. The cave-in portion 77 is formed on a circumferential edge of an opening end of the central terminal hole 75 on one side of the front side surrounding member 71 which accommodates the terminal metal fitting 51b having the protruding piece portion 54 which protrudes in a bifurcated fashion. Namely, in this embodiment, when the terminal metal fitting 51b is inserted into the terminal hole 75 with its front end facing the terminal hole 75 from a rear end side of the front side surrounding member 71 while the bifurcated protruding piece portion 54 is oriented radially outwards, the bifurcated portions of the protruding piece portion 54 are configured to fit in the cave-in portion 77 so as to abut a bottom thereof. In a state in which the protruding piece portion 54 is fit in the cave-in portion 77, the bifurcated portions of the protruding piece portion 54 are restrained by walls 77b of the cave-in portion 77 which face each other (see FIGS. 3, 4 and 7). This configuration, in which the protruding piece portion 54 of the terminal metal fitting 51b is fit in the cave-in portion 77 on the rear end face 73, restricts the terminal metal fitting 51b from rotating about its imaginary axis extending in the front-rear direction within the hole 75.

In this embodiment, the terminal connecting portions 53 of the terminal metal fittings 51a, 51b are accommodated in the terminal holes 75 in the front side surrounding member 71. Further, when the front end face 273 of the rear side surrounding member 271 abuts the rear end face 73 in that condition, the clamping portions 57a, 57b of the terminal metal fittings 51a, 51b are positioned within the terminal holes 275 in the rear side surrounding member 271. As this occurs, the protruding piece portions 54 are configured so as to be held between the bottoms of the cave-in portions 77 on the rear end face 73 of the front side surrounding member 71 and the front end face 273 of the rear side surrounding member 271. A depth of the cave-in portion 77 in the direction of the axis G is set so that the protruding piece portions 54 are held between the bottom surfaces of the cave-in portions 77 and the front end face 273 of the rear side surrounding member 271 when the rear end face 73 of the front side surrounding member 71 and the front end face 273 of the rear side surrounding member 271 abut each other.

In this embodiment, in addition to the cave-in portions 77, two recess portions 79 are provided on the rear end face 73 of the front side surrounding member 71 so as to be recessed towards the front end of the surrounding member 71 as shown in FIGS. 3 and 4. These recess portions 79 are arranged symmetrically with respect to the axis G in plan view, and are positioned close to an outer circumferential surface of the flange 74 so as to hold both edges of the element 21. On the other hand, protruding portions 279 are provided on the front end face 273 of the rear side surrounding member 271 so as to individually fit in the two recess portions 79. In such a state that the rear end face 73 of the front side surrounding member 71 abuts the rear end face 273 of the rear side surrounding member 271 with the terminal metal fittings 51a, 51b inserted into the corresponding holes 75, the protruding portions 279 fit in the recess portions 79 (see FIG. 11). This configuration prevents either of the front side surrounding member 71 and the rear side surrounding member 271 from rotating relative to the other about the axis G of the sensor 1. In this embodiment, both the recess portions and the protruding portions 279 have a fan-like shape as viewed from the direction of the axis G.

In the sensor 1 of the embodiment, the individual lead wires 61 are passed through individual through holes 105 provided in the sealing elastic member 101 which is compressed within a rear end (an upper end in FIG. 1) of the protective sleeve 81 so as to be pulled out of the rear end of the metallic protective sleeve 81 (see FIG. 1). The through holes 105 are formed substantially in the same arrangement as that of the terminal holes 275 provided in the rear side surrounding member 271. A rear end of the sealing elastic member 101 is configured to push a rear end of the rear side surrounding member 271 towards the front end side when compressed.

The cylindrical protective sleeve 81 having different diameters is disposed so as to surround the front side surrounding member 71 and the rear side surrounding member 271. The protective sleeve 81 has a sealing sleeve portion 83 at the rear end thereof via a ring-like shoulder portion 84 which extends continuously therefrom towards the axis G side. The sealing sleeve portion 83 is formed into a coaxial cylindrical shape whose diameter is relatively reduced, and the sealing elastic member 101 is disposed within the sealing sleeve portion 83. The protective sleeve 81 has a large diameter sleeve portion 82 which is larger in diameter than the sealing sleeve portion 83 in a position frontward (the lower end in the figure) of the sealing sleeve portion 83. The protective sleeve 81 is fitted on the cylindrical portion 15 positioned near the rear end of the metal shell 11, and is fixed to the main body 11 by welding after crimping an outer circumferential surface of the portion where the protective sleeve 81 is fitted on the cylindrical portion 15.

In this embodiment, a cylindrical supporting member 91 for supporting the terminal surrounding member whose rear end 93 is bent inwards in a fold-back fashion is disposed concentrically within an annular space defined between an inner circumferential surface of the large diameter sleeve portion 82 of the protective sleeve 81 and the front side surrounding member 71. Further, the cylindrical supporting member 91 is fixed to an inner surface of the protective sleeve 81. The supporting member 91 is made from a metallic plate (a thin plate) into a substantially cylindrical shape, and has a spring piece 95 which is formed by being bent in a fold-back fashion at the rear end 93 thereof. An intermediate portion 85 of the large diameter sleeve portion 82 of the protective sleeve 81 is crimped so as to reduce its diameter. The protective sleeve 81 is thereby deformed so that the diameter is reduced in the direction of the axis G. By means of this deformation, the spring piece 95 is pressed against an outer circumferential surface 72a of the front side surrounding member 71, whereby the front side surrounding member 71 is fixed in place within the protective sleeve 81. In this embodiment, the fold-back portion which constitutes the rear end (the upper end) 93 of the supporting member 91 is disposed so as to be locked on a surface of the flange 74 of the front side surrounding member 71 which is oriented towards the front end. This configuration prevents the front side surrounding member 71 from moving towards the front end side in an ensured fashion.

According to the sensor 1 of the embodiment configured as described above, the following advantage can be realized. Namely, in the sensor 1 of the embodiment, in the terminal metal fittings which are disposed on the respective sides of the element 21, the terminal metal fittings 51b which are positioned at the center in the width direction have the protruding piece portions 54. These protruding piece portions 54 are held in the front-rear direction by the rear end face 73 of the front side surrounding member 71 and the front end face 273 of the rear side surrounding member 271. Consequently, since this configuration prevents the terminal metal fittings 51b from moving not only in the rear direction but also in the front direction (towards the front end side) within the sensor 1, the positions of the terminal metal fittings 51b can be made stable in the front-rear direction. Further, the occurrence of electrical connection failures or contact failures between the terminal connecting portions 53 of the terminal metal fittings 51b and the electrode terminals 25 on the element 21 is effectively prevented.

In this embodiment, the protruding piece portion 54 of the terminal metal fittings 51b fits in the cave-in portion 77. Because of this, even when a rear end of the terminal metal fitting 51b or on the lead wire 61 which is connected thereto is twisted, an external force generated by the twisting action is stopped or absorbed by the protruding piece portion 54 that is retrained by the walls 77b of the cave-in portion 77. Consequently, this construction prevents the front side terminal connecting portion 53 (which extends continuously from the protruding portion 54) from rotating about the imaginary axis extending in the front-rear direction within the hole 75. Further, the occurrence of electrical connection failures between the terminal connecting portions 53 and the electrode terminals 25 of the element 21 can be prevented more effectively.

Moreover, according to sensor 1 of the embodiment, the front side surrounding member 71 and the rear side surrounding member 271 are fitted into each other as described above at the recess portions 79 and the protruding portions 279 which are provided on the end faces 73, 273, respectively. This construction prevents either of the front side surrounding member 71 and the rear side surrounding member 271 from rotating relative to the other about the axis G of the sensor 1. Further, reliable electrical connection between the terminal metal fittings 51b which have the protruding piece portions 54 and the electrode terminals 25 of the element 21 is further enhanced.

Figure 12:
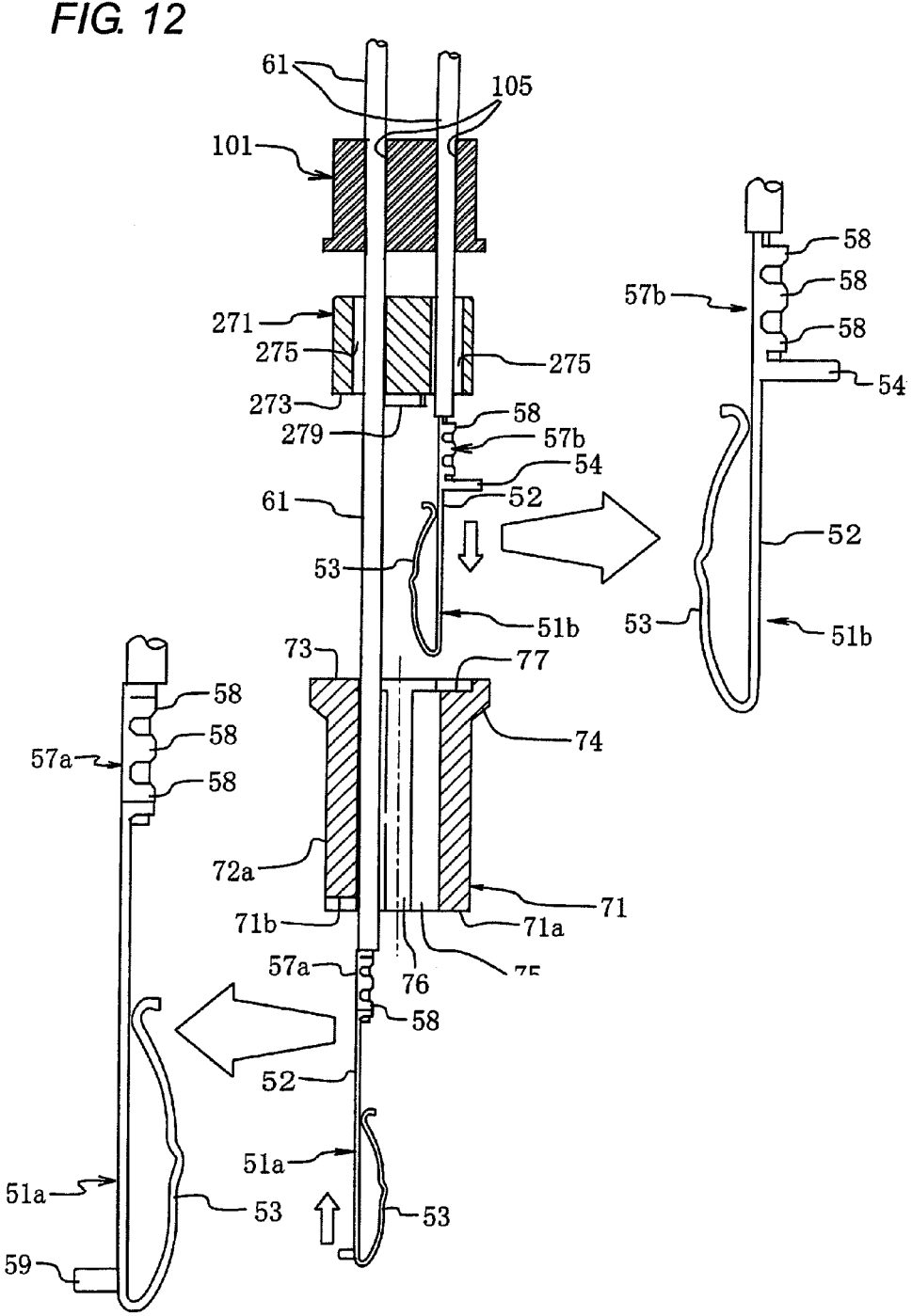
FIG. 12 is a drawing illustrating a step of fabricating the sensor of FIG. 1.

The terminal metal fitting side assembly half 301 shown at the top right part of FIG. 14 will be described below (see FIGS. 12 and 13). Namely, end portions (front ends) of the individual lead wires 61 are passed through the through holes 105 provided in the sealing elastic member 101 to allow passage of the lead wires 61. The lead wires 61 are also passed through the terminal holes 275 provided in the rear side surrounding member 271. As this occurs, the lead wires 61 other than the lead wires 61 connected to the central terminal metal fittings 51b are passed through the terminal holes 75 in the front side surrounding member 71. Then, the crimping pieces 58 which constitute the clamping portions 57a, 57b at the rear ends of the terminal metal fittings 51a, 51b are bent and crimped as described above so as to connect to core wire portions at the end portions of the individual lead wires 61 (see FIG. 12). As this occurs, as shown in FIG. 12, the terminal connecting portions 53 are guided so to be oriented towards the corresponding side surface 24 of the element 21.

The respective terminal connecting portions 53 of the terminal metal fittings are inserted into the corresponding terminal holes 75 in the front side surrounding member 71 so as to be arranged as described above, and the protruding piece portions 54 of the terminal metal fittings 51b are fitted in the cave-in portions 77 on the rear end face 73 of the front side surrounding member 71. Then, with the clamping portions 57a, 57b which protrude rearwardly of the front side surrounding member 71 inserted into the terminal holes 275 in the rear side surrounding member 271, the front end face 273 of the rear side surrounding member 271 abuts the rear end face 73 of the front side surrounding member 71. Following this, the rear end (the upper end in the figures) of the rear side surrounding member 271 is brought into contact with a front end (a lower end in the figures) of the sealing elastic member 101 (see FIG. 13).

Figure 13:
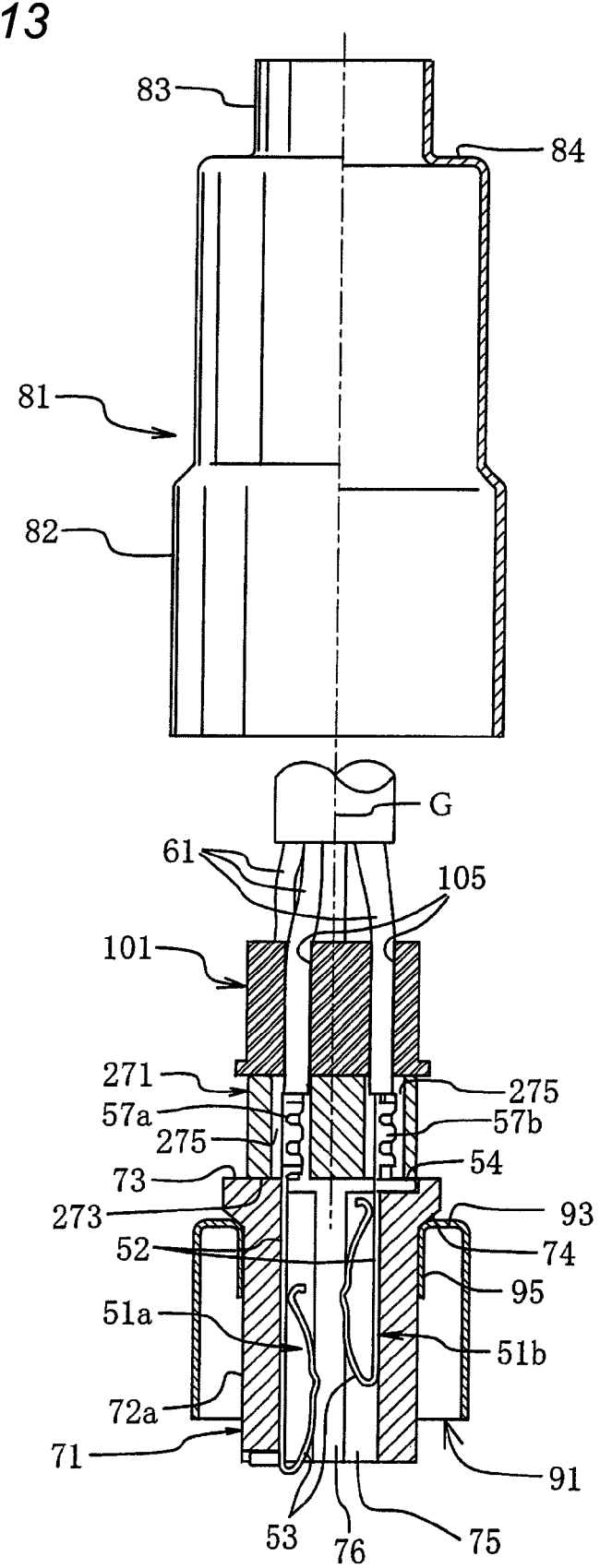
FIG. 13 is a drawing illustrating a step of fabricating the sensor of FIG. 1.

As shown in FIG. 13, the supporting member 91 is fitted on the outer circumferential surface 72a of the front side surrounding member 71 from a front end side (a lower side in the figure) thereof, and the rear end portion 93 of the supporting member 91 is brought into abutment with the surface of the flange 74 facing toward the front side so as to be attached thereto. Following this, the protective sleeve 81 is placed to surround the sealing elastic member 101, the rear side surrounding member 271 and the front side surrounding member 71 from the rear end side (from above in the figure). Next, with the protective sleeve 81 thus placed, the portion 85 on an outer circumferential surface of the large diameter sleeve portion 82 of the protective sleeve 81 which corresponds to an intermediate portion in the front-rear direction of the supporting member 91 is crimped so as to contract in diameter (so as to be drawn in). By this action, the terminal metal fitting side assembly half 301 shown at the top right part of FIG. 14 can be obtained.

Thereafter, axes G of both the assembly halves 201, 301 are aligned so that the rear portion 23 of the element 21 of the element side assembly half 201 is held by the terminal metal fittings 51a, 51b of the terminal metal fitting side assembly half 301 as shown in FIG. 14. Then, the assembly halves 201, 301 are made to approach each other, and the rear portion 23 of the element 21 is inserted between the facing terminal metal fittings 51a, 51b, so that their terminal connecting portions 53 are pressed against the electrode terminals 25 on the element 21. Next, a front end of the large diameter sleeve portion 82 of the protective sleeve 81 is fitted on the cylindrical portion 15 of the metal shell 11 which lies closer to the rear end thereof. Then, the fitting portion is crimped from the outer circumferential surface side and is thereafter fixed to the cylindrical portion 15 by welding. Finally, the sealing sleeve portion 83 at the rear end (the upper end in the figure) of the protective sleeve 81 is crimped so as to contract in diameter, whereby the sealing elastic member 101 is compressed in the radial direction so as to be fixed in place therein. Through this series of operations, the sensor 1 shown in FIG. 1 is obtained.

The sensor of the invention is not limited to the above embodiment, and can be modified as needed. In the sensor 1 of the embodiment, the protruding piece portions 54 are provided only on the terminal metal fittings 51b, which constitute part of the terminal metal fittings provided in the sensor 1, so as to be held between the rear end face 73 of the front side surrounding member 71 and the front end face 273 of the rear side surrounding member 271. However, all the terminal metal fittings may be configured in the same manner as the terminal metal fittings 51b. Further, lead wires of a gas sensor installed in a motor vehicle are used as wiring cables which are made up of bundles of wires like a wiring harness. Thus, even when protruding portions are provided on terminal metal fittings of only part of the lead wires so as to be held in the manner described above, a function of restricting the movement of the other terminal metal fittings can be obtained. From this fact, when embodying the invention, the number and/or arrangement of protruding piece portions may be set as required based on any of the number of lead wires, the form of a bundle of wires, the size of a terminal surrounding member and the like.

The shape, construction or size of the protruding piece portions may only have to be such as to resist a force that acts on the terminal metal fittings on which the protruding piece portions are provided in the front-rear direction, when held between the rear end face of the front side surrounding member and the front end face of the rear side surrounding member. Further, the protruding piece portions may only have to be set in accordance with the strength, thickness and the like of the terminal metal fittings. In addition, in the embodiment, while the protruding piece portions are fitted in the cave-in portions so as to be held between the rear end face of the front side surrounding member and the front end face of the rear side surrounding member, the protruding piece portions do not necessarily have to be fitted in the cave-in portions only to prevent the terminal metal fittings from moving in the front-rear direction.

Further, in the embodiment, while the cave-in portions are cave-in portions into which the protruding piece portions can fit and which can restrict the terminal metal fittings which have the protruding piece portions from rotating about the imaginary axes extending in the front-rear direction in the terminal holes, in this case, too, the shape and construction of the protruding piece portions or cave-in portions may only have to be set as required. Namely, this is because the shape and construction thereof may only have to be such as to resist a force as required which is generated upon twisting the rear ends of the terminal metal fittings on which the protruding piece portions are provided, with the protruding piece portions fitted in the cave-in portions. In addition, in the embodiment, while the cave-in portions are provided only on the rear end face of the front side surrounding member, the cave-in portions may be provided only on the front end face of the rear side surrounding member, and the cave-in portions may be provided so as to straddle between both end faces or on both end faces.

In the embodiment, in order to prevent either of the front side surrounding member and the rear side surrounding member from rotating relative to the other on the axis of the sensor, in such a state that the rear end face of the front side surrounding member abuts the front end face of the rear side surrounding member, one or more recess portions (e.g., recess portion 71) are formed on the rear end face and one or more protruding portions (e.g., protruding portion 279) are formed on the front end face, so that corresponding recess portions and protruding portions fit into each other. However, the protruding portions and the recess portions may be provided on either of the end faces.

Thus, as described above, the sensor of the invention can be embodied by making appropriate modifications without departing from the spirit and scope of the claims appended thereto. For example, in the embodiment above, while the three electrode terminals are described as being provided on each of the side surfaces of the element, the number of electrode terminals is not limited thereto. In addition, in the embodiment, while the invention is embodied as a gas sensor, the sensor of the invention can also be embodied as another type of sensor such as a temperature sensor.

This application is based on Japanese Patent Application No. 2008-313928 filed Dec. 10, 2008, the above application incorporated herein by reference in its entirety.

What is claimed is:

1. A sensor extending in a front-rear direction from a front end to a rear end thereof, said sensor comprising:
   a sensor element extending in the front-rear direction of the sensor and comprising a plurality of electrode terminals;
   a plurality of terminal metal fittings pressed against and connected to respective electrode terminals of the sensor element;
   a terminal surrounding member made of an insulating material and having terminal holes in which the respective terminal metal fittings extend in the front-rear direction, so as to surround the plurality of terminal metal fittings; and
   a plurality of lead wires connected to the respective terminal metal fittings and which are led out from the rear end of the sensor to an outside thereof,
   wherein the terminal surrounding member is divided into a front side surrounding member and a rear side surrounding member in the front-rear direction, and a rear end face of the front side surrounding member abuts a front end face of the rear side surrounding member,
   wherein at least one of the terminal metal fittings comprises a protruding piece portion protruding in a lateral direction and held between the rear end face of the front side surrounding member and the front end face of the rear side surrounding member.

2. The sensor according to claim 1,
   wherein at least one of the rear end face of the front side surrounding member and the front end face of the rear side surrounding member has a cave-in portion in which the protruding piece portion is fitted so as to restrict the terminal metal fitting comprising the protruding piece portion from rotating around an imaginary axis extending in the front-rear direction within the terminal hole.

3. The sensor according to claim 1,
   wherein a protruding portion is formed at one of the front side surrounding member and the rear side surrounding member, a recess portion is formed on the other of the front side surrounding member and the rear side surrounding member, and the protruding portion is fitted in the recess portion, whereby the rear end face of the front side surrounding member and the front end face of the rear side surrounding member abut each other so as to prevent one of the front side surrounding member and the rear side surrounding member from rotating relative to the other about an axis of the sensor.

* * * * *